(12) United States Patent
Bohlmann et al.

(10) Patent No.: US 7,392,708 B2
(45) Date of Patent: Jul. 1, 2008

(54) APPARATUS AND METHOD OF MEASURING SHEAR STRAIN OF THICK ADHESIVE BONDLINES

(75) Inventors: Raymond E. Bohlmann, Creve Coeur, MO (US); Milton D. Hurd, Cool Valley, MO (US); Jeff Wollschlager, Maryland Heights, MO (US)

(73) Assignee: The Boeing Company, Chicago, IL (US)

( * ) Notice: Subject to any disclaimer, the term of this patent is extended or adjusted under 35 U.S.C. 154(b) by 114 days.

(21) Appl. No.: 11/123,655

(22) Filed: May 6, 2005

(65) Prior Publication Data

US 2006/0248959 A1  Nov. 9, 2006

(51) Int. Cl.
  *G01N 3/24*  (2006.01)
(52) U.S. Cl. .................... 73/841; 73/150 A; 73/827; 73/842; 73/856
(58) Field of Classification Search .............. 73/841, 73/150 A, 827, 842, 856
See application file for complete search history.

(56) References Cited

U.S. PATENT DOCUMENTS

| 4,522,066 | A | * | 6/1985 | Kistler et al. ............... 73/781 |
| 4,848,161 | A | * | 7/1989 | van der Kuur ............. 73/760 |
| 5,119,569 | A | * | 6/1992 | Meline ....................... 33/790 |
| 5,275,057 | A | * | 1/1994 | Alexander .................. 73/799 |
| 5,335,547 | A | * | 8/1994 | Nakajima et al. ........... 73/622 |
| 5,361,640 | A | * | 11/1994 | Carroll et al. .............. 73/831 |

OTHER PUBLICATIONS

L.E. Crocker and G.D. Dean. Tensile Testing of Adhesive Buss-joint Specimens. "http://midas.npl.co.uk/midas/content/ma09.html" May 2001.*
"Evaluation and Adjustments for ASTM D 5656 Standard Test Method for Thick-Adherend Metal Lap-Shear Joints for Determination of the Stress-Strain Behavior of Adhesives in Shear by Tension Loading", Yang et al., American Chemical Society, 2001, pp. 36-43.
"Shear Stress-Strain Data for Structural Adhesives", Tomblin et al., U.S. Department of Transportation, Federal Aviation Administration, Final Report, Nov. 2002.
"Characterization of Bondline Thickness Effects in Adhesive Joints", Tomblin et al., Journal of Composites Technology & Research, 2002, pp. 80-92.
"Model 632.02 Clip-On Gage", MTS Systems Corporation 2001, 2 pages.

* cited by examiner

*Primary Examiner*—Edward Lefkowitz
*Assistant Examiner*—Freddie Kirkland, III
(74) *Attorney, Agent, or Firm*—Wildman, Harrold, Allen & Dixon, LLP

(57) ABSTRACT

A method an apparatus for testing shear strain response of a test specimen having a thick adhesive bond line is disclosed. Method and apparatus permit the use of readily available clip-on extensometers. The apparatus and method may include the use of knife edges secured to each of two adherend components on a standard ASTM D 5656 thick adherent test specimen.

14 Claims, 5 Drawing Sheets

APPARATUS AND METHOD OF MEASURING SHEAR STRAIN OF THICK ADHESIVE BONDLINES

This invention was made with Government support under contract number SCRA 2001-508 awarded by the United States Navy. The Government has certain rights in this invention.

BACKGROUND OF THE INVENTION

1. Field of the Invention

The invention is related to systems and methods for measuring shear stress-strain response, and more specifically, to systems and methods for measuring shear stress-strain response for structures that include thick adhesive bondlines.

2. Description of the Related Art

The standard method (ASTM D5656) that is typically used to measure the shear stress-strain response for thin adhesive bondlines (e.g., having bondline thicknesses of 0.005 to 0.020 in or 0.127 to 0.508 mm) employs the American Cyanamid KGR-1 gage. One improvement to ASTM D5656 has been proposed in Yang et al., "Evaluation and Adjustments for ASTM D5656 Standard Test Method for Thick-Adherend Metal Lap-Shear Joints for Determination of the Stress-Strain Behavior of Adhesives in Shear by Tension Loading," Journal of Testing and Evaluation, JTEVA, volume 29, no. 1, January 2001, pp. 36-43. In this article, the authors set forth an arrangement that uses four pins and mounting holes to mount a KGR-1 device to a test specimen, to reduce errors due to slippage of the mounting pins. However, the KGR-1 gage has limited deflection travel (d=0.020 in., see FIG. 1a) and was designed for use in testing of bondline thicknesses ($t_a$) less than 0.040 in. and therefore cannot be used for testing of thick bondlines.

This disclosure is directed toward overcoming one or more problems or disadvantages associated with the prior art.

SUMMARY OF THE INVENTION

According to one aspect of the invention, a method of testing shear strain response of a test specimen having a thick adhesive bond line disposed between two adherend components is provided. The method includes providing a first pair of knife edges secured to each of two sides of a first adherend component, providing a second pair of knife edges secured to each of two sides of a second adherend component, applying a tensile load to the first and second adherend components, and measuring a displacement of the first and second pairs of knife edges with respect to one another.

In accordance with another aspect of the invention, shear strain response of thick adhesive bondlines may be measured using standard clip-on extensometers.

The features, functions, and advantages can be achieved independently in various embodiments of the present invention or may be combined in yet other embodiments.

DETAILED DESCRIPTION

Figure 1:
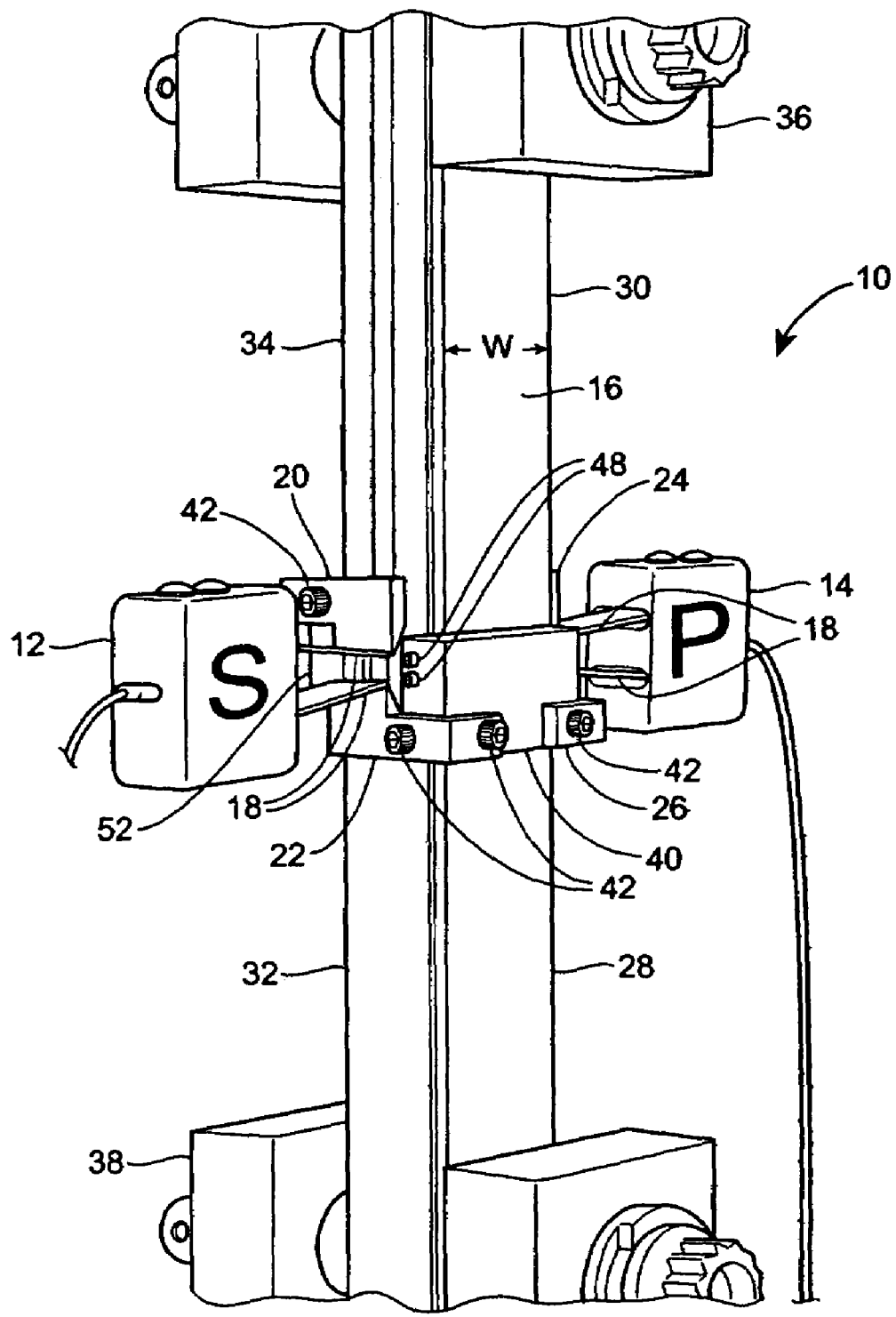
FIG. 1 is a diagrammatic prospective view of a test apparatus according to one exemplary embodiment of the disclosure.

With reference to initially to FIG. 1, a test apparatus 10 for measuring shear strain response of thick adhesive bondlines may include a first extensometer 12, a second extensometer 14, and a test specimen 16. The test specimen 16 may be constructed in accordance with ASTM D5656 and may have a width, W, of 1.0 in (2.54 cm). The first and second extensometers 12 and 14 may be clip-on type extensometers, such as, for example, MTS model 632.02 clip-on gages, available from MTS Systems Corporation.

The first and second extensometers 12 and 14 may each include a pair of cantilevers 18 that engage a starboard upper knife edge component 20 on the starboard side of the test specimen 16, a lower starboard knife edge component 22 on the lower starboard side of the test specimen 16, an upper port knife edge component 24, on the port side of the test specimen 16, and a lower port knife edge component 26 on the lower port side of the test specimen 16.

The test specimen 16 may include a lower front adherend component 28, an upper front adherend component 30, a lower rear adherend component 32, and an upper rear adherend component 34 (shown in isolation in FIG. 2), that may each be made from a metallic material (e.g., 6A1-4V Titanium). The test specimen 16 may be, for example, attached to a tension testing machine by upper and lower pinned joints 36 and 38.

Figure 2:
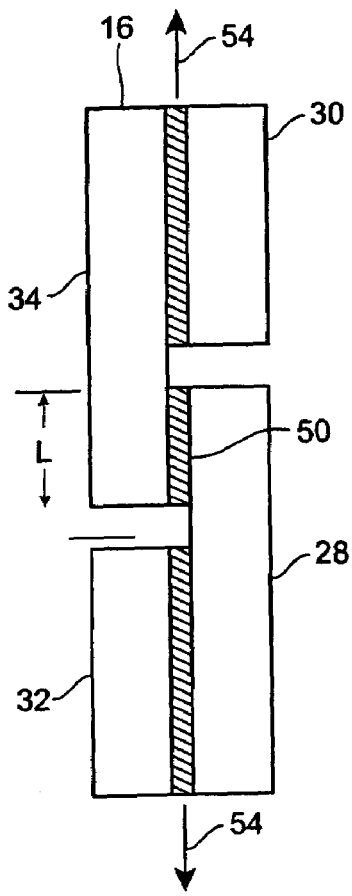
FIG. 2 a diagrammatic side view of a test specimen that may be used in the test apparatus of FIG. 1.

As shown in FIG. 2, the test specimen 16 may be constructed in order to obtain a measurement of shear strain response of a thick adhesive bond line 50 when the test specimen 16 is subjected to a tensile load, as indicated by the arrows 54 in FIG. 2.

Figure 3:
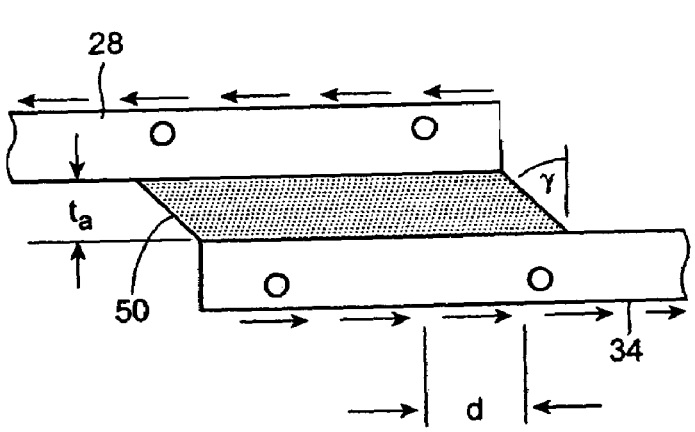
FIG. 3 is an enlarged diagrammetric opposing side view of a portion of the test specimen of FIG. 2.
Figure 4:
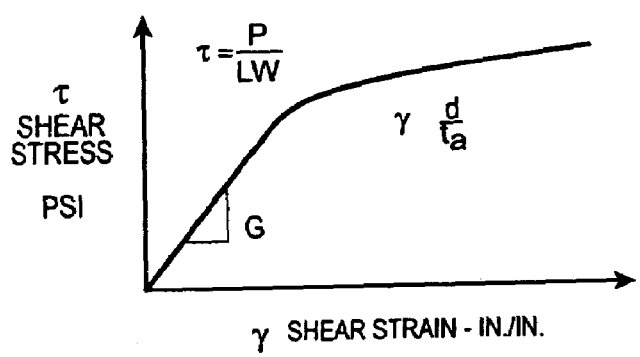
FIG. 4 is a graphical representation of a typical stress-strain curve.

In operation, the test apparatus 10 permits the use of simple clip-on extensometers to measure shear strain response of the thick adhesive bond line 50, by providing knife edge surfaces from which shear displacement may be measured. With reference to FIG. 3, this testing methodology has a deflection capability of d=0.15 in. or (8 times greater than KGR-1) and can accept a bondline thickness of $t_a$=0.30 in. or (~8 times greater than KGR-1). The important adhesive design data obtained from this test is the shearing strain (gamma, FIG. 4) obtained at failure which is a measure of the adhesive ductility and is obtained by dividing the maximum deflection travel (d) by the adhesive thickness ($t_a$), see FIG. 1a. Also, unlike with the KGR-1 gage, the new method does not require the use of a metal correction factor due to the location of the set screws 48 (FIG. 1), therefore eliminating the need for a metal correction test specimen as specified in ASTM D5656. The test equipment should have capability to measure a ultimate shearing strain of 1.0 in./in.

Each of the four knife edge components 20, 22, 24, and 26 may be attached to the test specimen 16 in any suitable fashion.

For example, each of the lower knife edge components 26 and 22 may be secured to a lower channel member 40 by threaded fasteners 42 that pass through end bores 44 and side bores 46 formed in the lower knife edge components 22 and 26 (the bores 44 and 46 are best seen in FIGS. 5-10). The lower channel member 40 may be attached to the lower front adherend component 28, for example, by set screws 48 (FIG. 1), that pass through set screw bores 52 (shown in FIG. 1).

Figure 5:
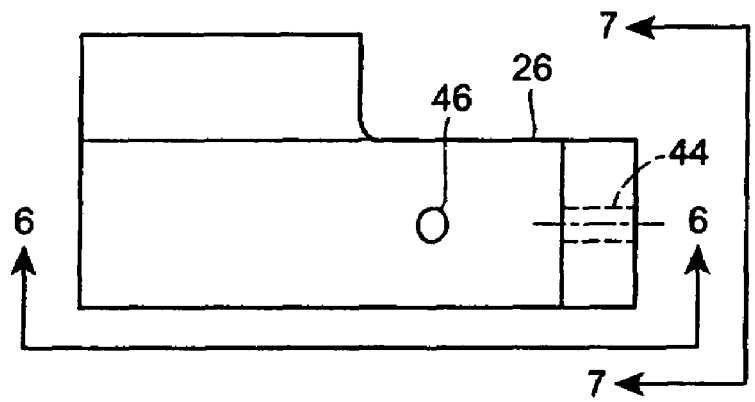
FIG. 5 is a diagrammatic side view of a knife edge component that may be used in the test apparatus of FIG. 1.
Figure 6:
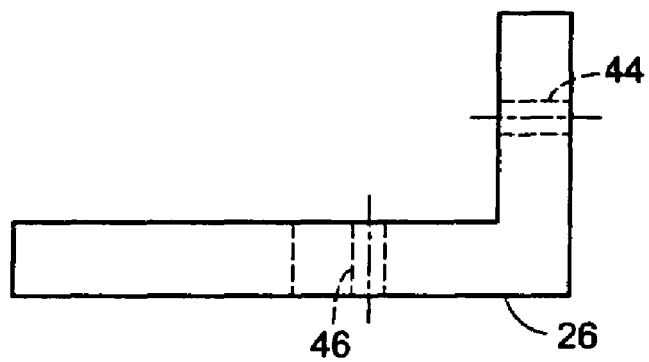
FIG. 6 is a bottom view, taken along lines 6-6 of FIG. 5 of the knife edge component of FIG. 5.
Figure 7:
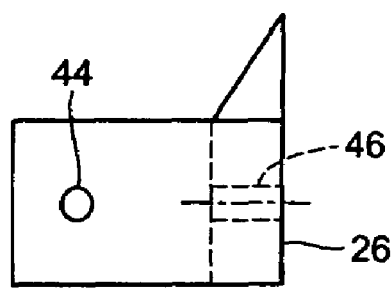
FIG. 7 is an end view, taken along lines 7-7 of FIG. 5, of the knife edge component of FIG. 5.

FIGS. 5-7 show the lower port knife edge component 26 in isolation. As best seen in FIG. 6, the lower port knife edge component 26 may have a substantially L-shaped geometry when viewed from below. The upper port knife edge component 24 may have identical geometry to that of the lower port knife edge component 26. Accordingly, it is not necessary to show the upper port knife edge component 24 in isolation.

Figure 8:
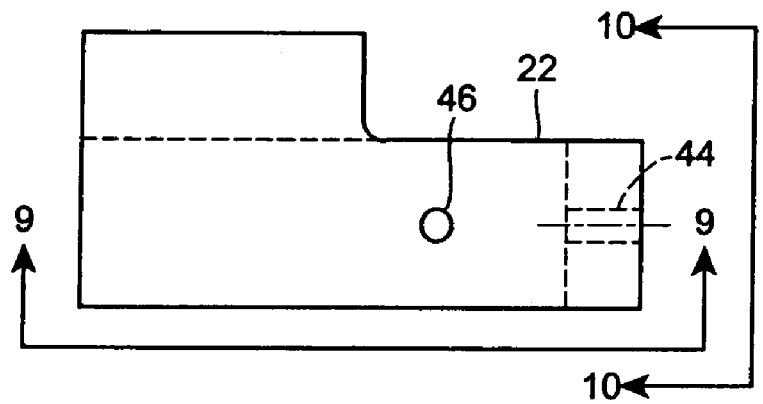
FIG. 8 is a diagrammatic side view of another knife edge component that may be used in the apparatus of FIG. 1.
Figure 9:
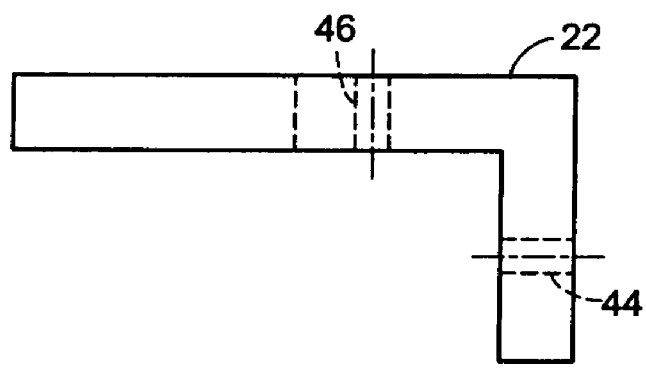
FIG. 9 is a bottom view taken along lines 9-9 of FIG. 8, of the knife edge component of FIG. 8.
Figure 10:
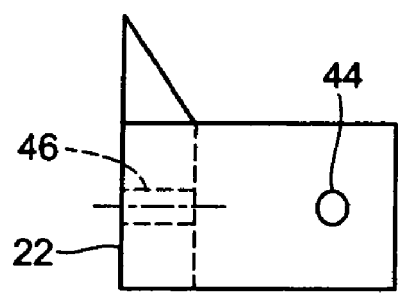
FIG. 10 is a diagrammatic end view, taken along lines 10-10 of FIG. 8, of the knife edge component of FIG. 8.

Similarly, FIGS. 8-10 show the lower starboard knife edge component 22 in isolation, and the upper starboard knife edge component 20 may have identical geometry to that of the lower starboard knife edge component 22.

Figure 11:
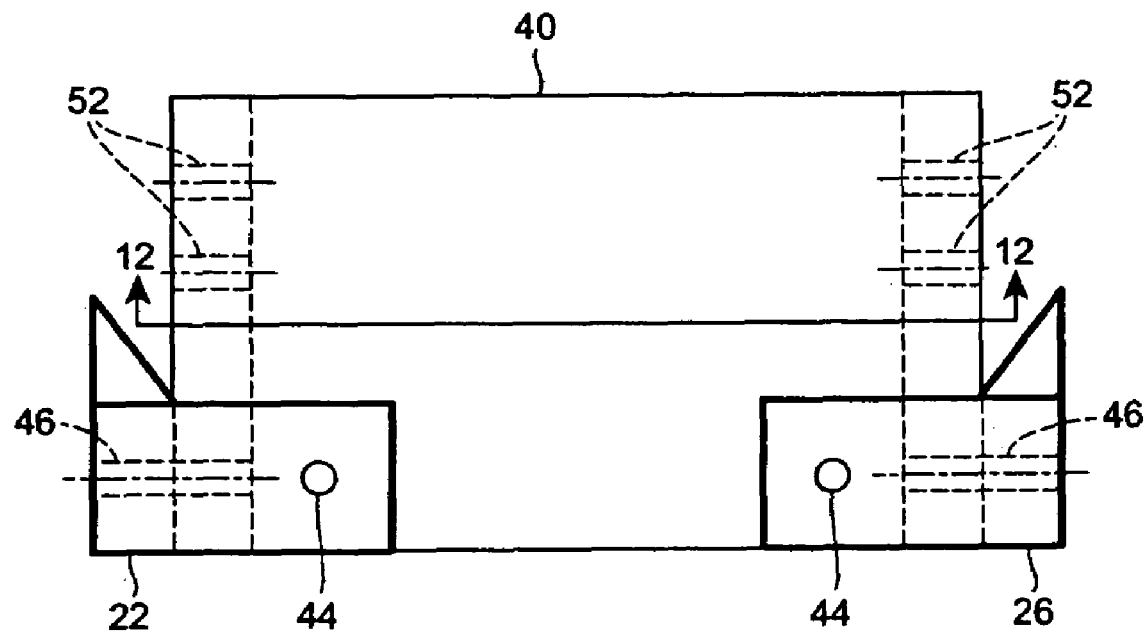
FIG. 11 is a diagrammatic front view of the knife edge components of FIGS. 5-10, attached to a channel member.
Figure 12:
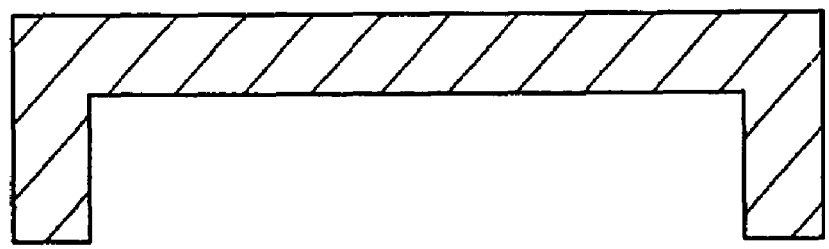
FIG. 12 is a diagrammatic cross-sectional view of the channel member, taken along lines 12-12 of FIG. 11.

FIG. 11 shows the placement of the lower knife component 26 and 22 on the lower channel member 40, and FIG. 12 is a cross-sectional view of the channel member 40.

Other aspects and features of the present invention can be obtained from a study of the drawings, the disclosure, and the appended claims.

What is claimed is:

1. A method of testing shear strain response of a test specimen having an adhesive bondline disposed between two adherend components, the method comprising:
   providing a first pair of knife edges secured to each of two sides of a first adherend component;
   providing a second pair of knife edges secured to each of two sides of a second adherend component;
   wherein the first and second pairs of knife edges are secured to at least one channel-shaped member disposed between the first and second pairs of knife edges and the test specimen;
   applying a tensile load to the first and second adherend components; and
   measuring a displacement of the first and second pairs of knife edges with respect to one another, wherein the method is adapted to test shear strain responses of test specimens having thin adhesive bondlines, and the method is also adapted to test shear strain responses of test specimens having thick adhesive bondlines up to 0.30 inches.

2. The method of claim 1 wherein the step of measuring a displacement of the first and second pairs of knife edges with respect to one another is done utilizing at least one extensometer.

3. The method of claim 1 wherein the knife edges are secured to the test specimen using threaded fasteners.

4. The method of claim 1 wherein the knife edges are constructed from a metallic material.

5. The method of claim 4 wherein the metallic material is steel.

6. An apparatus for testing shear strain response of a test specimen having an adhesive bondline disposed between two adherend components, the apparatus comprising:
   a first pair of knife edges secured to each of two sides of a first adherend component;
   a second pair of knife edges secured to each of two sides of a second adherend component; and
   the first and second pairs of knife edges are secured to at least one channel-shaped member disposed between the first and second pairs of knife edges and the test specimen, wherein the apparatus is adapted to test shear strain responses of test specimens having thin adhesive bondlines, and the apparatus is also adapted to test shear strain responses of test specimens having thick adhesive bondlines up to 0.30 inches.

7. The apparatus of claim 6, wherein the knife edges are constructed from a metallic material.

8. The apparatus of claim 7, wherein the metallic material is steel.

9. The system of claim 6, wherein the knife edges are secured to the test specimen using threaded fasteners.

10. The apparatus of claim 6 wherein at least one extensometer is disposed between the first and second pairs of knife edges.

11. An apparatus for testing shear strain response of a test specimen having an adhesive bondline disposed between two adherend components, the apparatus comprising:
    a first pair of knife edges secured to each of two sides of a first adherend component;
    a second pair of knife edges secured to each of two sides of a second adherend component;
    the first and second pairs of knife edges are secured to at least one channel-shaped member disposed between the first and second pairs of knife edges and the test specimen; and
    at least one extensometer disposed between the first and second pairs of knife edges, wherein the apparatus is adapted to test shear strain responses of test specimens having thin adhesive bondlines, and the apparatus is also adapted to test shear strain responses of test specimens having thick adhesive bondlines up to 0.30 inches.

12. The apparatus of claim 11 wherein the knife edges are secured to the test specimen using threaded fasteners.

13. The apparatus of claim 11 wherein the knife edges are constructed from a metallic material.

14. The apparatus of claim 13 wherein the metallic material is steel.

\* \* \* \* \*